(12) United States Patent
Huang

(10) Patent No.: US 9,364,298 B2
(45) Date of Patent: Jun. 14, 2016

(54) ORTHODONTIC BRACKET HAVING A BIASED SLIDE MEMBER

(71) Applicant: Ormco Corporation, Orange, CA (US)

(72) Inventor: Stanley S. Huang, Irvine, CA (US)

(73) Assignee: Ormco Corporation, Orange, CA (US)

( * ) Notice: Subject to any disclaimer, the term of this patent is extended or adjusted under 35 U.S.C. 154(b) by 64 days.

(21) Appl. No.: 14/072,310

(22) Filed: Nov. 5, 2013

(65) Prior Publication Data

US 2014/0127638 A1    May 8, 2014

Related U.S. Application Data

(60) Provisional application No. 61/724,273, filed on Nov. 8, 2012.

(51) Int. Cl.
*A61C 7/20* (2006.01)
*A61C 7/28* (2006.01)
*A61C 7/30* (2006.01)

(52) U.S. Cl.
CPC .. *A61C 7/287* (2013.01); *A61C 7/30* (2013.01)

(58) Field of Classification Search
CPC ....................................................... A61C 7/287
USPC ........................................................... 433/11
See application file for complete search history.

(56) References Cited

U.S. PATENT DOCUMENTS

| 5,094,614 | A |   | 3/1992 | Wildman |
| 5,275,557 | A |   | 1/1994 | Damon |
| 5,322,435 | A | * | 6/1994 | Pletcher ........................... 433/11 |
| 5,356,288 | A |   | 10/1994 | Cohen |
| 5,466,151 | A |   | 11/1995 | Damon |
| 5,474,445 | A |   | 12/1995 | Voudouris |
| 5,857,849 | A |   | 1/1999 | Kurz |
| 5,857,850 | A |   | 1/1999 | Voudouris |
| 5,971,753 | A |   | 10/1999 | Heiser |
| 6,071,118 | A |   | 6/2000 | Damon |

(Continued)

FOREIGN PATENT DOCUMENTS

EP        1508310 A2    2/2005
WO    2012145144 A1    10/2012

OTHER PUBLICATIONS

European Patent Office, European Search Report in EP13191984.7 dated Mar. 3, 2014.

(Continued)

*Primary Examiner* — Ralph Lewis
(74) *Attorney, Agent, or Firm* — Wood, Herron & Evans, LLP

(57) ABSTRACT

An orthodontic bracket includes a bracket body, a slide member, and a resilient member. The slide member is slidable relative to the archwire slot. The resilient member is coupled to and is slidable with the slide member. The resilient member is configured to engage a first portion of the bracket body in the opened position and a second portion of the bracket body in the closed position. The second portion is different from the first portion. The resilient member imposes a biasing force on the slide member in the direction of movement toward the archwire slot when the slide member is in the closed position. The resilient member may be configured to impose a biasing force on the slide member in the direction away from the archwire slot when the slide member is at a position intermediate the opened and closed positions.

19 Claims, 13 Drawing Sheets

(56) References Cited

U.S. PATENT DOCUMENTS

| | | | |
|---|---|---|---|
| 7,416,408 B2* | 8/2008 | Farzin-Nia et al. | 433/10 |
| 7,621,743 B2* | 11/2009 | Bathen et al. | 433/10 |
| 8,033,824 B2* | 10/2011 | Oda et al. | 433/11 |
| 8,251,696 B2* | 8/2012 | Rodriguez et al. | 433/10 |
| 8,998,607 B2* | 4/2015 | Oda | A61C 7/30 433/10 |
| 2006/0154196 A1 | 7/2006 | Oda | |
| 2007/0248928 A1* | 10/2007 | Damon | 433/10 |
| 2007/0269763 A1 | 11/2007 | Schendell-Groling | |
| 2008/0045956 A1 | 2/2008 | Songer et al. | |
| 2010/0285420 A1* | 11/2010 | Oda | 433/11 |
| 2012/0129119 A1* | 5/2012 | Oda | A61C 7/30 433/11 |

OTHER PUBLICATIONS

European Patent Office, European Search Report in EP14159463.0 dated Jul. 1, 2014.

* cited by examiner

ORTHODONTIC BRACKET HAVING A BIASED SLIDE MEMBER

CROSS-REFERENCE TO RELATED APPLICATIONS

This application claims priority to U.S. Provisional Patent Application Ser. No. 61/724,273 filed Nov. 8, 2012, the disclosure of which is incorporated by reference herein in its entirety.

TECHNICAL FIELD

The invention relates generally to orthodontic brackets and, more particularly, to self-ligating orthodontic brackets having movable closure members.

BACKGROUND

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While such self-ligating brackets are generally successful in achieving their intended purpose, there remain some drawbacks. By way of example, in some instances controlling the rotation of the teeth, such as near the finishing stages of orthodontic treatment, can be problematic. While there may be several factors that cause a reduction in rotational control, it is believed that one of the major causes is the loose fit of the archwire within the archwire slot of the bracket when the movable member is closed. When the movable member is closed, the bracket body and the movable member collectively form a closed lumen for capturing the archwire. A close fit between the lumen and the archwire is believed to be important for achieving excellent rotational control during orthodontic treatment.

The close fit between the archwire and the archwire slot when the movable member is closed may be affected by several factors including, for example, the tolerances of the manufacturing process used to form the bracket body and the movable member. When the orthodontic bracket is assembled, the various tolerances may "stack up" so as to provide a relatively loose fit between the archwire and the closed lumen provided by the bracket body and movable member. As noted above, such a loose fit is believed to result in a diminished capacity to control the rotation of the teeth. In addition, to allow the movable member to move relative to the bracket body between the opened and closed positions, there must be some clearance between the bracket body and the movable member. In other words, there are typically some tolerances in the manufacturing that provide a clearance. Yet, these tolerances stack up to provide a lumen which may vary significantly in its labial-lingual dimension between brackets and therefore may provide a relatively loose fit with the archwire in some instances.

Thus, while self-ligating brackets have been generally successful, manufacturers of such brackets continually strive to improve their use and functionality. In this regard, there remains a need for self-ligating orthodontic brackets that provide improved rotational control during orthodontic treatment, such as during the finishing stages thereof.

SUMMARY

An orthodontic bracket that addresses these and other shortcomings of existing brackets includes a bracket body configured to be mounted to the tooth. The bracket body has an archwire slot configured to receive the archwire. A slide member is slidable relative to the archwire slot between an opened position and a closed position. The orthodontic bracket includes a resilient member that is coupled to and is slidable with the slide member. The resilient member is configured to engage a first portion of the bracket body when the slide member is in the opened position and a second portion of the bracket body when the slide member is in the closed position. The second portion of the bracket body is different from the first portion of the bracket body. The resilient member is configured to impose a biasing force on the slide member in the direction of movement of the slide member toward the archwire slot when the slide member is in the closed position.

In one embodiment, the resilient member is configured to impose a biasing force on the slide member in the direction of movement of the slide member away from the archwire slot when the slide member is at a position intermediate the opened position and the closed position.

In one embodiment, the slide member includes a bore configured to receive one portion of the resilient member, and the bracket body includes an aperture configured to receive another portion of the resilient member. The axis of the portion of the resilient member in the bore is offset from the axis of the resilient member in the aperture when the slide member is in the closed position.

In one embodiment, the bracket body further includes an aperture that is asymmetric about a plane substantially parallel to the archwire slot and is configured to slidably receive the resilient member.

In one embodiment, the aperture includes the first portion and the second portion of the bracket body. The first portion is separated from the second portion by a pinch point that restricts passage of the resilient member during sliding movement thereof.

In one embodiment, the first portion is separated from the second portion by a central portion. A first radius defines the first portion, and a second radius defines the second portion. The central portion includes a first segment and a second segment opposing the first segment. The first segment is tangent to the first radius and is tangent to the second radius. The second segment is tangent to the first radius and is transverse to the first segment.

In one embodiment, a projection of the second segment intersects the first segment or a projection thereof at a location between the first portion and the archwire slot and forms an angle with the first segment of equal to or less than about 60°.

In one embodiment, a projection of the second segment intersects the first segment or a projection thereof and forms an angle with the first segment of between about 10° and about 30°.

In one embodiment, the bracket body includes a dovetail-shaped portion and the slide member includes a central portion configured to receive the dovetail-shaped portion. The dovetail-shaped portion and the central portion are configured to form an interference fit that limits movement of the slide member in a direction away from the tooth when the slide member is at least in the closed position.

In one embodiment, the archwire slot includes a base surface and a first slot surface and a second opposing slot surface that each extends outwardly from the base surface. The bracket body includes an aperture that defines a slide track along which the resilient member is slidable. A projection of the slide track forms an acute angle with the base surface or a projection thereof.

In one embodiment, the slide member has a leading surface and, when the slide member is in the closed position, a gap is formed between the leading surface and one of the first slot surface and the second slot surface.

In one embodiment, the bracket body further includes a shoulder that is oriented at a transverse angle relative to the slide track, and the slide member abuts the shoulder when the slide member is in the closed position.

In one embodiment, the shoulder is parallel to the base surface of the archwire slot.

In one embodiment, the slide member has a leading surface and the slide member abuts the shoulder which prevents the leading surface from contacting an opposing portion of the bracket body.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
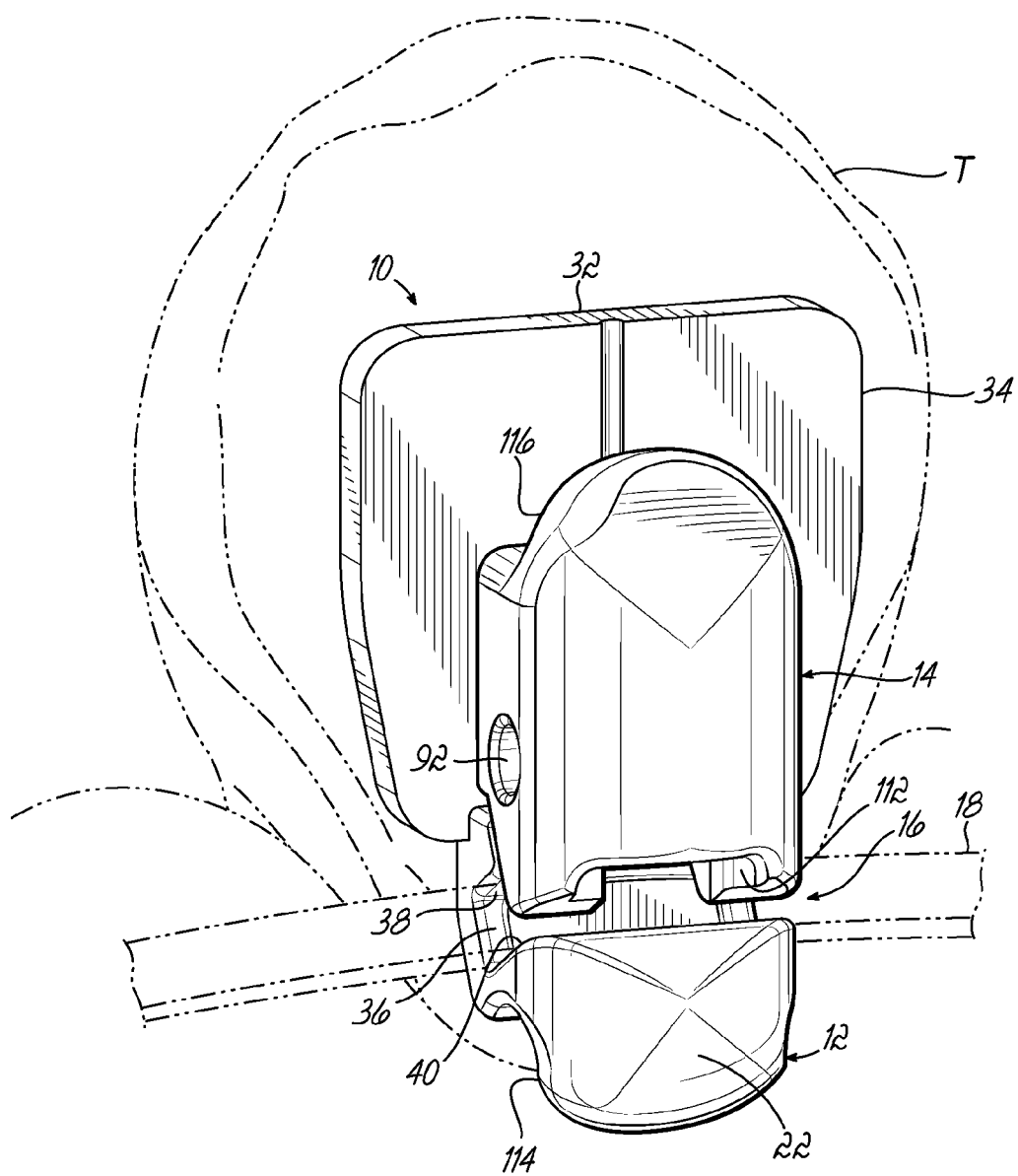
FIG. 1 is a perspective view of an orthodontic bracket according to one embodiment of the invention attached to a tooth, a slide member shown in the closed position.
Figure 2:
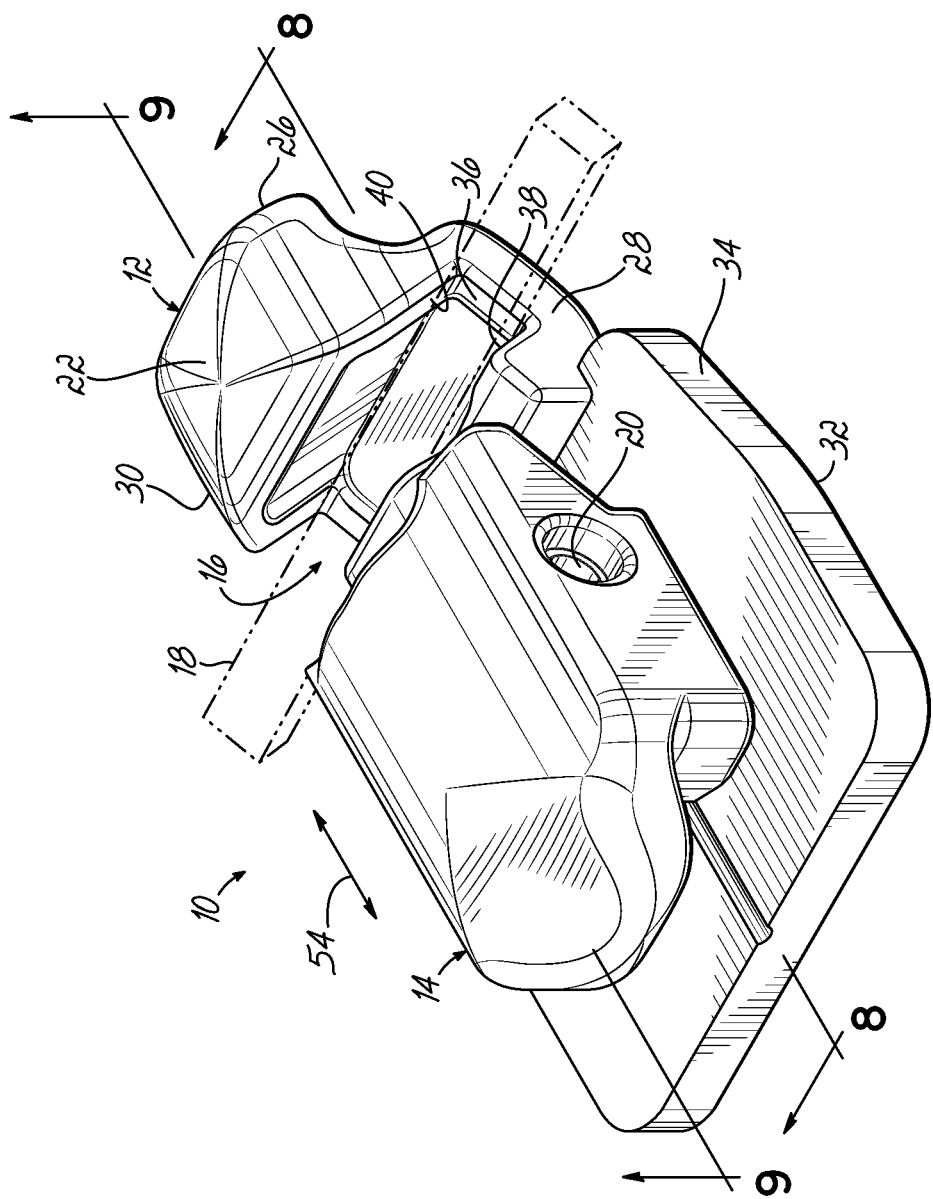
FIG. 2 is a perspective view of the orthodontic bracket shown in FIG. 1 with the slide member shown in the opened position.

Referring now to the drawings, and to FIGS. 1 and 2 in particular, an orthodontic bracket 10 includes a bracket body 12 and a movable closure member coupled to the bracket body 12. In one embodiment, the movable closure member may include a slide member or a ligating slide 14 slidably coupled with the bracket body 12. The bracket body 12 includes an archwire slot 16 formed therein configured to receive an archwire 18 (shown in phantom) for applying corrective forces to the teeth. The ligating slide 14 is movable between a closed position (FIG. 1) in which the archwire 18 is retained within the archwire slot 16, and an opened position (FIG. 2) in which the archwire 18 is insertable into the archwire slot 16. The bracket body 12 and ligating slide 14 collectively form an orthodontic bracket 10 for use in corrective orthodontic treatments.

In addition to the above, the orthodontic bracket 10 further includes a resilient member coupled to the ligating slide 14 and configured to engage at least a portion of the bracket body 12. As explained in more detail below, the resilient member, which in one embodiment includes a tubular pin 20 (shown in FIG. 2), provides a force for biasing the ligating slide 14 in the direction of the sliding or translational motion of the ligating slide 14. While the resilient member is shown herein as a tubular pin, the invention is not limited to this particular configuration, as other resilient members may be configured in accordance with the invention disclosed herein. It is believed that providing a biasing force in conjunction with the structural features of the orthodontic bracket 10, as described below, reduces the effects of tolerance variations of the archwire slot 16. By limiting the tolerance variation, the working dimensions of the archwire slot 16 may be more precisely known. This ultimately allows the clinician to more precisely predict and control tooth movement with the orthodontic bracket 10. It will be appreciated that improving the clinician's control of tooth movement may comparatively reduce treatment time for a particular patient.

The orthodontic bracket 10, unless otherwise indicated, is described herein using a reference frame attached to a lingual surface of an anterior tooth on the lower jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the labial surface of the tooth and be within the scope of the invention. Those of ordinary skill in the art will recognize that the descriptive terms used herein may not directly apply when there is a change in reference frame. Nevertheless, embodiments of the invention are intended to be independent of location and orientation within the oral cavity and the relative terms used to describe embodiments of the orthodontic bracket are to merely provide a clear description of the embodiments in the drawings. As such, the relative terms labial, lingual, mesial, distal, occlusal, and gingival are in no way limiting the invention to a particular location or orientation.

Figure 3:
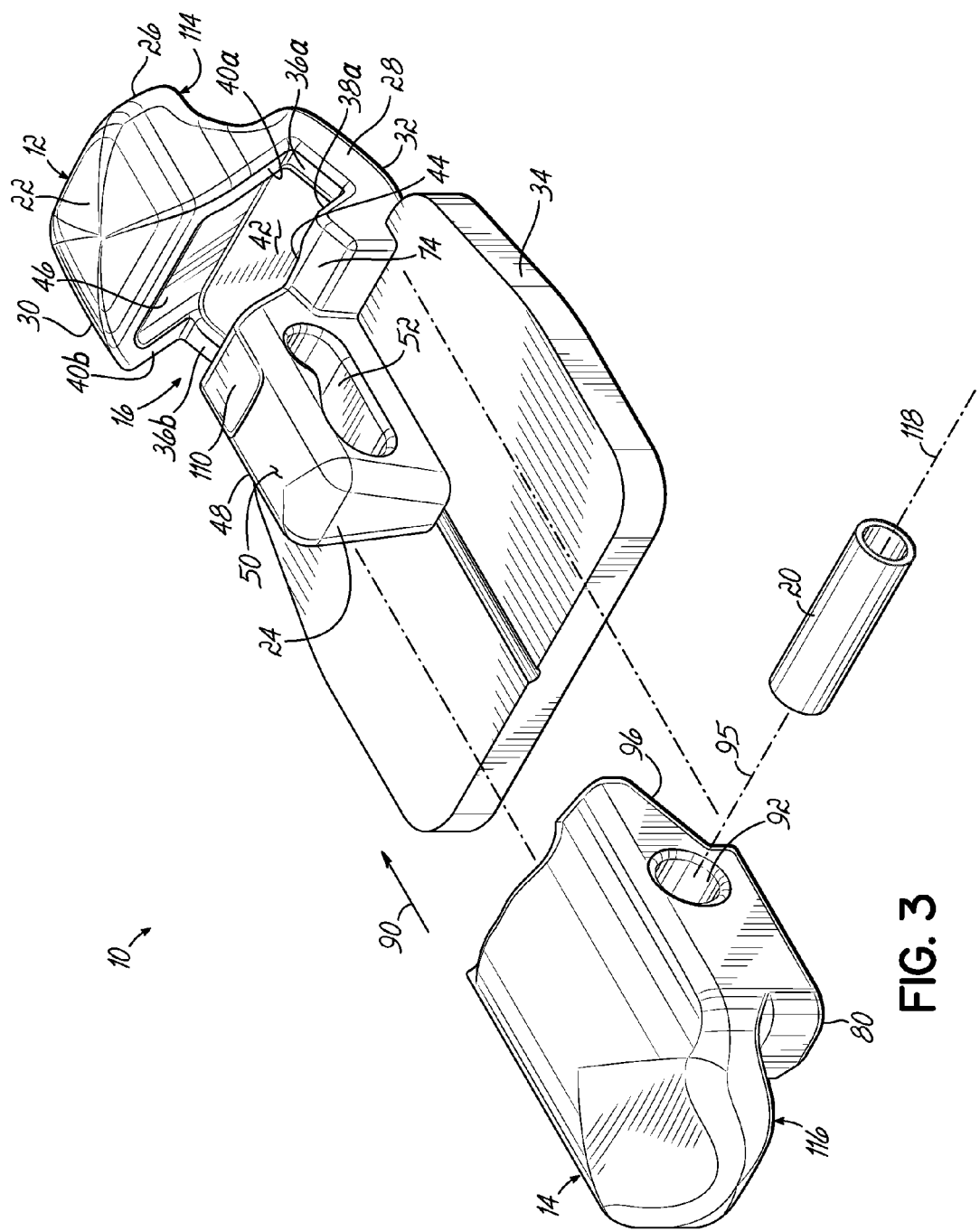
FIG. 3 is an exploded perspective view of the orthodontic bracket shown in FIG. 2.

When mounted to the lingual surface of a tooth T carried on the patient's lower jaw (shown in FIG. 1) and with reference specifically to FIG. 3, the bracket body 12 has a lingual side 22, an occlusal side 24, a gingival side 26, a mesial side 28, a distal side 30, and a labial side 32. The labial side 32 of the bracket body 12 is configured to be secured to the tooth in any conventional manner, such as for example, by an appropriate orthodontic cement or adhesive or by a band around an adjacent tooth. In one embodiment shown in FIGS. 1-3, the labial side 32 may further be provided with a pad 34 defining a bonding base that is secured to the surface of the tooth T. The pad 34 may be coupled to the bracket body 12 as a separate piece or element, or alternatively, the pad 34 may be integrally formed with the bracket body 12. Further, the pad 34 may be specifically shaped to fit on the surface of a particular lingual tooth surface. The pad 34 may therefore have a multitude of configurations different from that shown in FIGS. 1-3. It will be appreciated that embodiments of the present invention are not limited to any particular configuration of the pad 34.

With reference to FIGS. 1 and 2, the bracket body 12 includes a base surface 36 and a pair of opposed slot surfaces 38, 40 projecting lingually from the base surface 36 that collectively define the archwire slot 16, which may extend in a mesial-distal direction from mesial side 28 to distal side 30. The base surface 36 and slot surfaces 38, 40 are substantially encapsulated or embedded within the material of the bracket body 12. In one embodiment, one or more of the base surface 36 and slot surfaces 38, 40 are defined by corresponding rails 36a, 36b, 38a, 38b, 40a, and 40b which may be separated by corresponding recesses 42, 44, and 46. It will be appreciated that any single pair of rails 36a and 36b, 38a and 38b, and 40a and 40b (FIG. 3) may provide two points of contact between the bracket body 12 and the archwire 18 along the corresponding archwire slot surfaces 36, 38, and 40.

As shown in FIG. 3, in one embodiment, the bracket body 12 further includes a slide support portion 48 configured to receive the ligating slide 14 thereon. The slide support portion 48 may generally project lingually from or be oriented perpendicular to the pad 34. The slide support portion 48 defines a support surface 50 to slidably engage the ligating slide 14 over at least a portion of its translational motion from the closed position to the opened position. In a lingual application, as shown in FIG. 1, the support surface 50 is positioned occlusally of the archwire slot 16 and extends in a generally occlusal-gingival direction.

Figure 4:
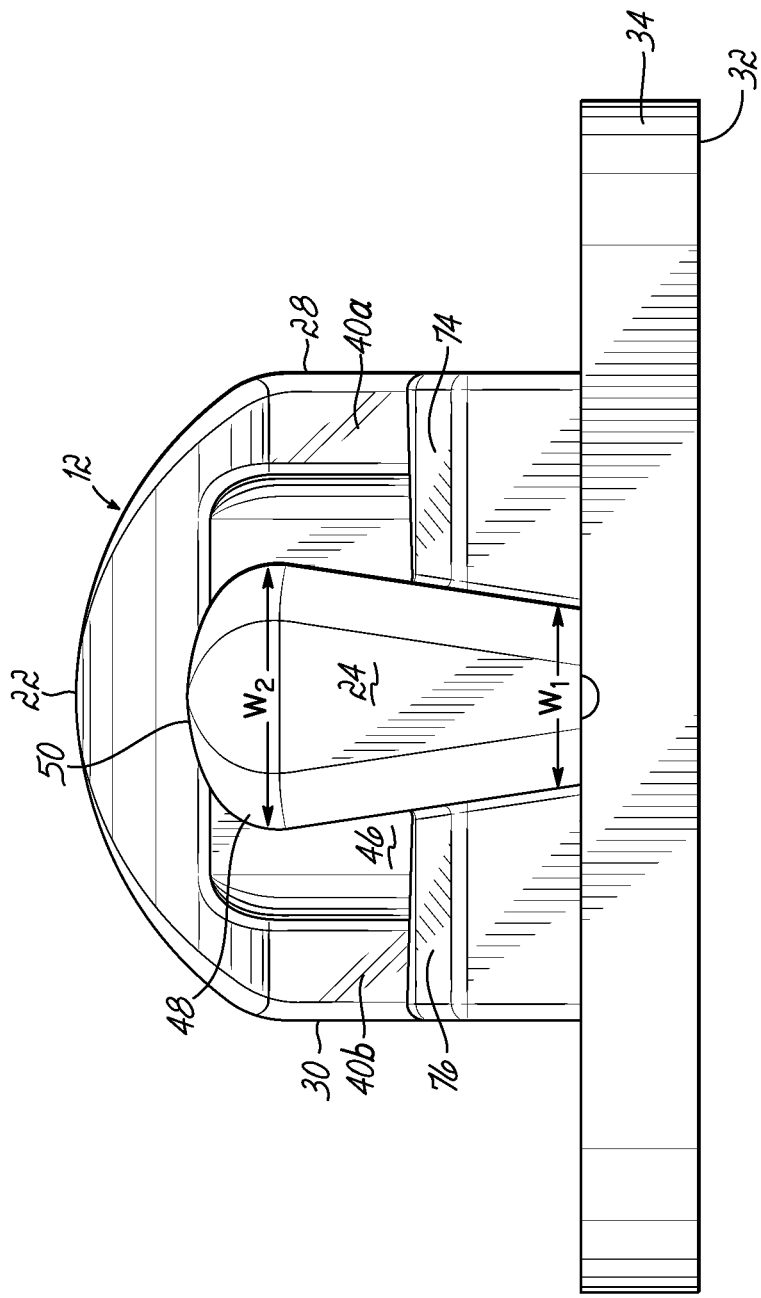
FIG. 4 is a front elevation view of the orthodontic bracket body shown in FIG. 3.

With reference now to FIG. 4, the slide support portion 48 may be tapered in the labial-lingual direction. In the configuration shown, the slide support portion 48 may have a first mesial-distal width, W1, at a location proximate the pad 34 and a second mesial-distal width, W2, proximate the support surface 50. The width W2 may be greater than the width W1 to form a wedge or dovetail shape. The dovetail shape may inhibit or resist labial-lingual movement of the slide 14 relative to the bracket body 12 due to an interference fit between the width W2 and a narrowest dimension of a channel in the slide 14, as is described in more detail below. It is believed that the wedge-shaped configuration of the slide support portion 48 may aid in the retention of the ligating slide 14 on the bracket body 12 in the event that the resilient member 20 fails in some manner. While the support surface 50 may have an arcuate configuration, as shown, the support surface 50 may be planar or have other configurations without departing from the invention as disclosed herein.

Figure 5:
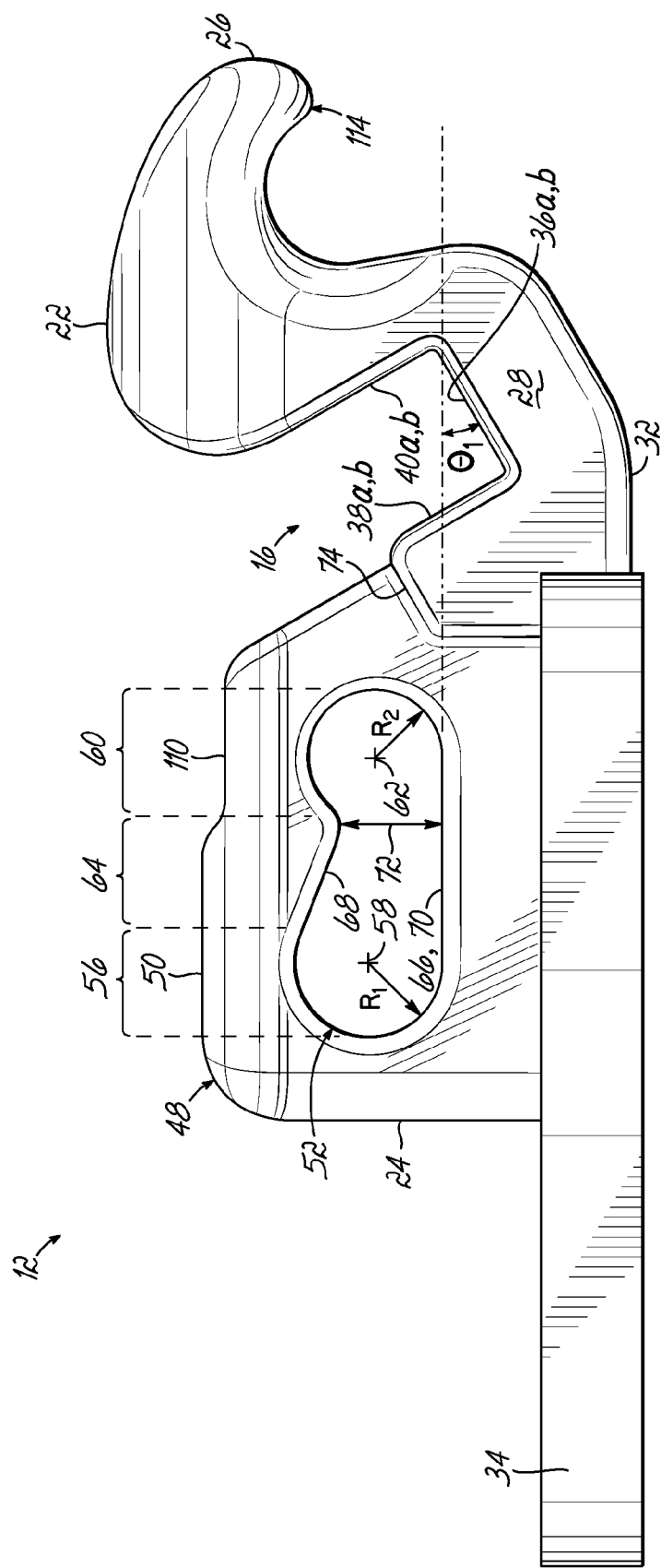
FIG. 5 is a side elevation view of the orthodontic bracket body shown in FIG. 3.

With reference to FIG. 5, the slide support portion 48 includes an aperture 52 formed as a through bore in the mesial-distal direction. The aperture 52 may be positioned so that the longitudinal axis of the resilient member 20 extends generally parallel with the archwire slot 16 and in the mesial-distal direction. In one embodiment, the aperture 52 is a generally asymmetrical bore about a plane that is perpendicular to the direction of slide motion as indicated by arrow 54 shown in FIG. 2. The aperture 52 may be described as having an irregular configuration.

As will be described in detail below, the aperture 52 is configured to slidably engage the resilient member 20 to bias the ligating slide 14 in the direction of slide translational movement. In particular, when the slide 14 is in the closed position, as is shown in FIG. 1, the aperture 52 in conjunction with the resilient member 20 and the slide 14 produces a net force on the slide 14 in the gingival direction (e.g., in the closed direction). This net force must then be overcome, in addition to other forces described below, before the slide 14 can be moved away from the closed position or, according to FIG. 1, in the occlusal direction or toward the opened position. The net force maintains the slide 14 in a fixed, more stable position relative to the bracket body 12 thereby maintaining a more consistent labial-lingual archwire slot dimension. In other words, stack up tolerances in the labial-lingual direction are reduced or eliminated.

As shown in FIG. 5, the aperture 52 may include a first lobe portion 56 proximate the occlusal side 24. By way of example only, the first lobe portion 56 may define a generally circular perimeter along a portion of the aperture 52. The lobe portion 56 may be defined by an axis 58 and a radius R1. The aperture 52 may further include a second lobe portion 60 proximate the archwire slot 16. Similar to the first lobe portion 56, the second lobe portion 60 may be defined by a generally circular perimeter having axis 62 and a radius R2.

In one embodiment, the aperture 52 may include a central portion 64 positioned between and connecting the first lobe portion 56 and the second lobe portion 60. The central portion 64 may include a first segment 66 that is tangent to the first lobe portion 56 and that is also tangent to the second lobe portion 60. The first lobe portion 56, the second lobe portion 60 and the first segment 66 may generally define a slide track 70 for the resilient member 20. As is generally indicated in FIG. 5, a projection of the slide track 70 may form an acute angle θ1 with the base surface 36 of the archwire slot 16.

In addition, the central portion 64 may include a second segment 68 opposite the first segment 66. The second segment 68 may be tangent to the first lobe portion 56, but may extend in a direction such that an extension of the second segment 68 would intersect (rather than be tangent to) the second lobe portion 60. By further extending the second segment 68, it intersects the first segment 66. The angle formed between the first and second segments 66, 68 may be equal to or less than about 60° and may depend on a particular tooth onto which the bracket 10 is to be affixed. By way of example, the second segment 68 may be angled at between about 10° and about 30° with respect to the first segment 66, and by way of further example, the second segment 68 may be angled from about 19° to about 21° with respect to the first segment 66.

In one embodiment, the orientation of the first segment 66 and the second segment 68 of the central portion 64 forms a restriction or pinch point 72 between the first lobe portion 56 and the second lobe portion 60. The pinch point 72 is generally a narrowing of the aperture 52 between the first and second lobe portions 56, 60. This may include narrowing of the aperture 52 to a dimension that is less than each of the largest height (or labial-lingual) dimensions for the first and second lobe portions 56, 60. By way of example only and not limitation, where each of the first and second lobe portions 56, 60 generally define circular bores having radii R1 and R2, respectively, the pinch point 72 may be measured as a perpendicular distance between the first segment 66 and the nearest opposing portion of the central portion 64. This perpendicular distance may be less than the diameter of the first lobe portion 56 or less than the diameter of the second lobe portion 60 or less than each of the diameters of the first lobe portion 56 and the second lobe portion 60. Further, this dimension may be at least 5% less or in the range of about 10% to about 20% less than either diameter of the first or second lobe portions 56, 60. In one embodiment, the radius R2 is less than the radius R1 and the pinch point 72 is sized to be less than twice R2. By way of example and not limitation, radius R2 may be about 5% to about 15% less than radius R1. In an exemplary embodiment, the radius R1 may be about 0.010 inches and the radius R2 may be about 0.009 inches and the pinch point 72 may measure about 0.017 inches.

As set forth above, the aperture 52 may be asymmetric. The asymmetry may be a result of the pinch point 72 being offset from a halfway point of the overall length of the aperture 52. As shown in FIG. 5, pinch point 72 is shifted toward the second lobe portion 60. Based on this shift alone, the aperture 52 is asymmetric about a plane that forms a perpendicular bisector of the overall length of the aperture 52. In addition, in embodiments where the first and second lobe portions 56, 60 are generally circular, the difference in corresponding radius dimension also produces asymmetry in the aperture 52. The asymmetry in the aperture 52 may produce a distinctive tactile response in the movement of the slide 14. In particular, as set forth in detail below, the asymmetry in the aperture 52 may provide the clinician with a distinctive "click" or "snap" to indicate that the slide 14 is in closed position.

With continued reference to FIGS. 4 and 5, in one embodiment of the invention, the bracket body 12 has at least one shoulder 74 oriented at an angle relative to the slide track 70. The shoulder 74 may extend in a generally mesial or distal direction from the slide support portion 48. It will be appreciated, however, that embodiments are not limited to the shoulder 74 in the configuration shown. In this regard, surfaces that abut the slide 14 may include another surface that has at least a component thereof oriented perpendicular to the slide track 70.

Figure 7:
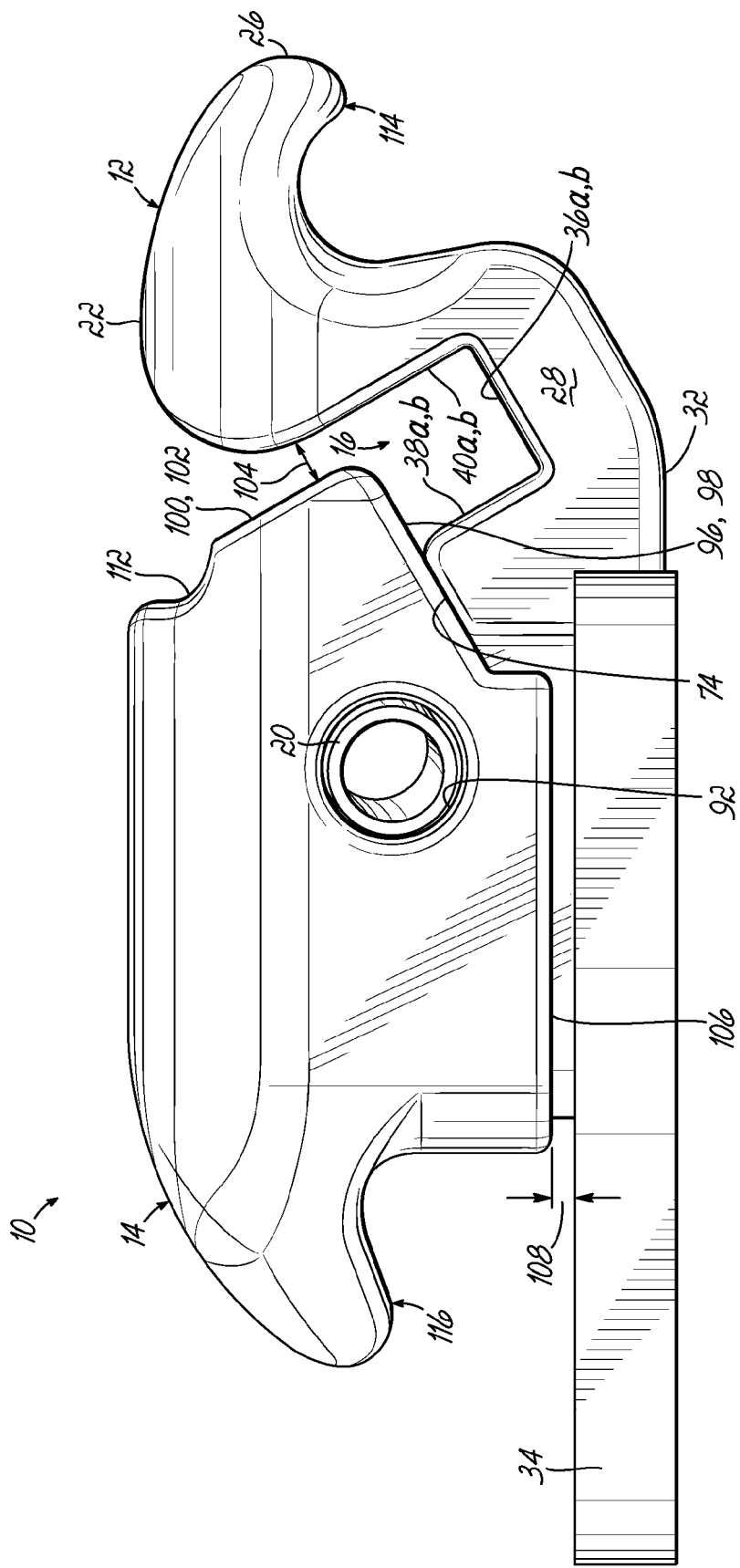
FIG. 7 is a side elevation view of the orthodontic bracket shown in FIG. 1.

In the exemplary embodiment shown, there are two shoulders, that is, a mesial shoulder 74 and a distal shoulder 76. One shoulder 74, 76 extends from each side of the slide support portion 48. With reference to FIGS. 4 and 5, the mesial shoulder 74 and distal shoulder 76 are angled relative to the slide track 70 and generally face in the occlusal direction. By way of example, the relative orientation of one or both of the shoulders 74, 76 may be similar to or the same as that of the base surface 36 relative to the slide track 70. In one embodiment, each shoulder 74, 76 is generally parallel with the base surface 36. As is shown in FIG. 7, one or more of the shoulders 74, 76 may form a stop against which the slide 14 resides when it is in the closed position.

Figure 6:
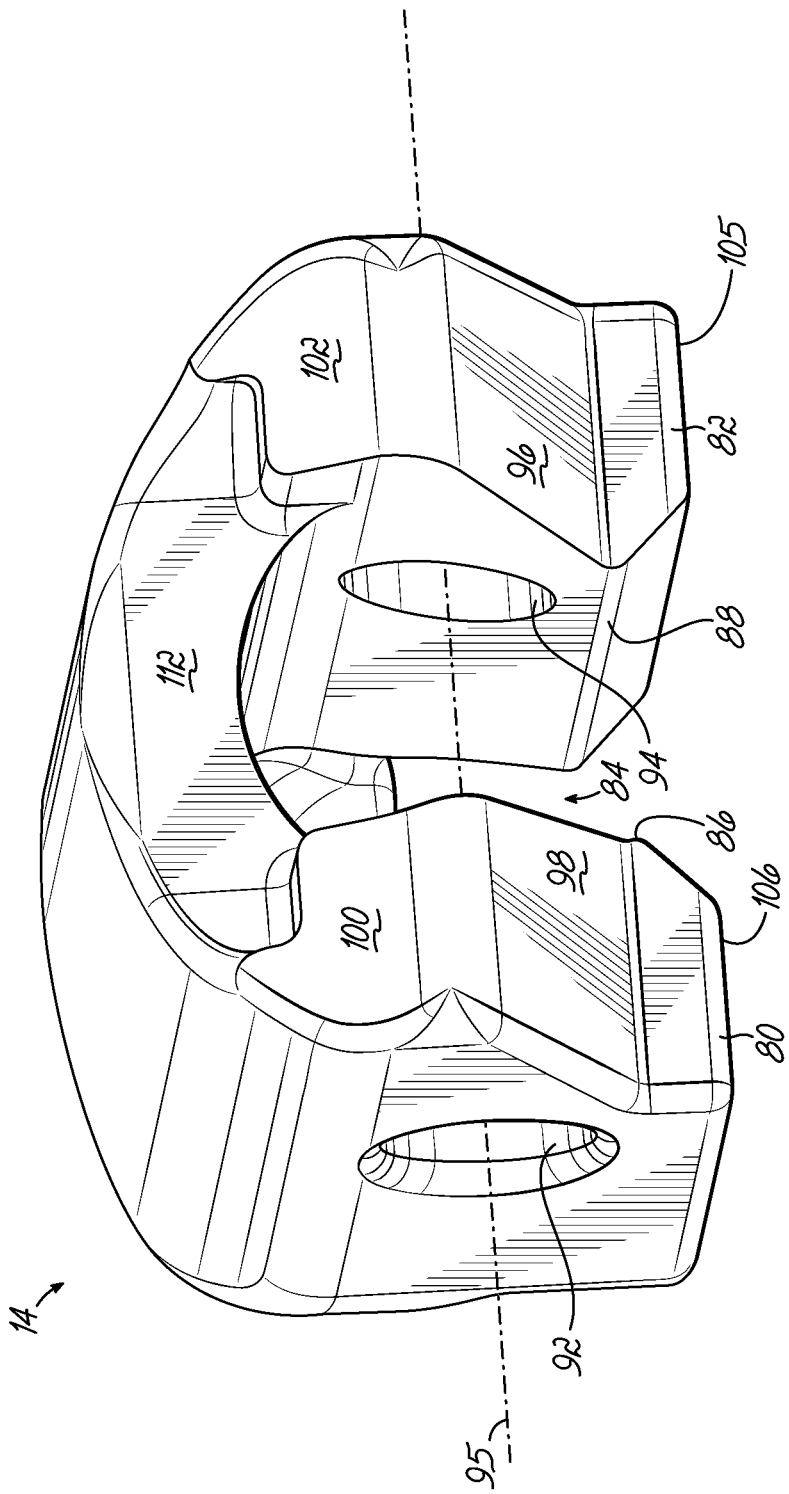
FIG. 6 is a perspective view of the slide member shown in FIG. 3.

With reference to FIGS. 3 and 6, the ligating slide 14 is generally a U-shaped configuration. The ligating slide 14 includes a first leg or mesial portion 80 and second leg or a distal portion 82 that generally define a slide channel 84 therebetween. The slide channel 84 is dimensioned to slidably cooperate with the slide support portion 48. In one embodiment, as shown in FIG. 6, the slide channel 84 is narrowest at opposing projections 86, 88 adjacent the labial-most edge of each of the mesial and distal portions 80, 82. The slide channel 84 may therefore have a wedge shaped or dovetail configuration that compliments or corresponds to the shape of the slide support portion 48 of the bracket body 12.

In one embodiment, the distance between the projections 86, 88 is less than the width W2 of the slide support portion 48 (shown in FIG. 4) but is slightly greater than width W1. In this case, the slide 14 is assembled with the bracket body 12 by a sliding motion from beyond the occlusal side 24 of the bracket body 12 in a direction toward the archwire slot 16. This is generally indicated in FIG. 3 by arrow 90. As set forth above, the wedge-shaped or dovetail configuration of the slide support portion 48, in cooperation with the similarly wedge-shaped or dovetail configuration of the slide channel 84, may inhibit or eliminate instances where the slide 14 accidentally disengages from the bracket body 12 in an outward or lingual direction in the event that the resilient member 20 fails.

With reference to FIG. 6, each of the mesial and distal portions 80, 82 includes at least one through bore that receives the resilient member 20. As shown, the mesial portion 80 includes a mesial through bore 92 and the distal portion 82 includes a distal through bore 94. The bores 92, 94 share a common axis 95. As shown in FIG. 3, the resilient member 20 is positioned in through bore 92 and through the aperture 52 and into the opposing bore 94 along axis 95. By this construction, the resilient member 20 may provide a mechanism for securing the ligating slide 14 to the bracket body 12 in one or both of the opened and the closed positions. In one embodiment, the resilient member 20 cooperates with the bracket body 12, and more particularly extends through the aperture 52, to secure the slide 14 to the bracket body 12 in each of the opened and closed positions. It will be appreciated that the bore 92 and the bore 94 may be sized to be slightly larger than the diameter or equivalent dimension of the resilient member 20. By way of example, the bores 92, 94 may be about 0.002 inches larger in dimension than the largest corresponding outer dimension of the resilient member 20. By way of further example, the bores 92, 94 may measure from about 10% to about 20% larger than the corresponding outer dimension of the resilient member 20.

In one embodiment, the ligating slide 14 includes mesial and distal engagement portions 96 and 98 formed along the lingual-most portion of each of the mesial and distal portions 80 and 82, respectively. In one embodiment shown in FIGS. 1 and 7, portions of each of the engagement surfaces 96, 98 oppose the base surface 36 when the ligating slide 14 is in the closed position and thereby form a fourth side of the archwire slot 16. In this regard, in the embodiment shown in FIG. 1, the engagement surfaces 96, 98 form the lingual boundary of the archwire slot 16 to capture the archwire 18 in the archwire slot 16 during orthodontic treatment.

In addition, in one embodiment, the engagement surfaces 96, 98 abut the mesial and distal shoulders 74, 76 when the ligating slide 14 is in the closed position. As introduced above, the resilient member 20 may bias the slide 14 in the direction of translational motion of the slide 14. This may include biasing of the slide 14 in a direction toward the archwire slot 16. Because the ligating slide 14 may be biased by resilient member 20 in the direction of slide 14 motion, the tolerance variations in the ligating slide 14 are no longer relevant in setting the depth of the archwire slot 16 in the generally labial-lingual direction. This is because regardless of the magnitude of tolerance variation, the ligating slide 14 will always be engaged against the shoulders 74, 76 of the bracket body 12 during normal orthodontic treatment. Thus, the tolerance variation that must still be considered and monitored during manufacturing is the tolerance in the positioning of the shoulders 74, 76 relative to the base surface 36 of the archwire slot 16. Advantageously, this reduces the number of tolerances that stack up to ultimately determine the depth of the archwire slot 16 in the generally labial-lingual direction and thereby provides a more consistent fit between the lumen, created by the bracket body 12 and ligating slide 14, and the archwire 18. It is believed that rotational control of the teeth may be more consistently maintained and predictable during orthodontic treatment.

In addition, as is shown in each of FIGS. 1, 6, and 7, in one embodiment, the engagement surfaces 96, 98 do not extend the full width or perpendicular distance of the archwire slot 16. In this regard, mesial and distal portions 80, 82 further include generally lingually oriented leading surfaces 100, 102. In the embodiment shown, the leading surfaces 100, 102 do not abut the opposing surfaces of the bracket body 12, as is shown best in FIG. 7. For example, surfaces 100, 102 do not contact the opposing slot surface 40 or, when present, either of the rails 40a, 40b. Accordingly, there remains a gap 104 between the bracket body 12 and the ligating slide 14 at this location. The gap 104 may be intentional and necessary to assure that the ligating slide 14 is consistently positioned relative to the base surface 36 or, when present, relative to the rails 36a, 36b.

By building in a gap at this location, contact between the engagement surfaces 96, 98 of the ligating slide 14 and the shoulders 74, 76 of the bracket body 12 during treatment is more probable or likely. It will be appreciated that reducing the number of other points of contact between the ligating slide 14 and the bracket body 12 increases the likelihood that the ligating slide 14 is more consistently positioned relative to the bracket body 12. Specifically, limiting contact with other locations or providing a built-in gap at other locations increases the probability of consistent contact between the engagement surfaces 96, 98 and the shoulders 74, 76. By way of example, the gap 104 may be at least about 0.001 inches, and by way of further example, the gap 104 may measure in the range of about 0.001 inches to about 0.005 inches. It will be appreciated, however, that the maximum dimension of the gap 104 may only be limited by the minimum extension of the engagement surfaces 96, 98 required to capture the archwire 18 within the archwire slot 16.

With further reference to FIG. 6, another gap or clearance may be built in between the slide 14 in the bracket body 12. In one embodiment, each of the mesial and distal portions 80, 82 is defined by surfaces 105 and 106. As shown in FIG. 7, the surfaces 105 and 106 oppose the pad 34 but do not slidably engage or contact the pad 34 when the ligating slide 14 is in the closed position. In this regard, there is a built-in gap 108 between the ligating slide 14 and the pad 34. Specifically, between the surface 105 and the pad 34 and between the surface 106 and the pad 34. By way of example, and not limitation, the gap 108 may be similarly dimensioned as the gap 104 between the surfaces 100, 102 and the slot surface 40, as set out above. Specifically, the gap 108 may measure at least about 0.001 inches, and by way of further example, may measure from about 0.001 inches to about 0.005 inches when the ligating slide 14 is in the closed position.

In one embodiment, the slide 14 contacts the bracket body 12 along only two lingually oriented surfaces. One contact surface is the support surface 50 and the other surface is one of the shoulders 74 or 76. Where both shoulders 74, 76 contact the slide 14, there are only three surfaces of contact between the slide 14 and the bracket body 12. By providing only a limited number of contact points, the position of the slide 14 relative to the bracket body 12 is more consistent, as is set out above.

In one embodiment, as depicted in FIG. 5, the bracket body 12 includes a tool clearance recess 110. As shown in FIG. 5, the recess 110 is formed in the lingual surface of the slide support portion 48 adjacent the support surface 50. In this regard, the support surface 50 extends over only a portion of the slide support portion 48 with the recess 110 forming the remaining portion thereof. The recess 110 may be configured as a generally planar surface displaced labially from the support surface 50. The recess 110 cooperates with the slide 14 to provide clearance between the slide support portion 48 and a tool (not shown) for moving the slide 14 toward the opened position.

In this embodiment, and with reference to FIG. 6, the ligating slide 14 further includes a tool recess 112 formed in the leading surfaces 100, 102 and extending in a direction generally toward the occlusal side 24. The tool recess 112 provides a region of increased clearance between the slide 14 and the bracket body 12 when the slide 14 is in the closed position. The tool recess 112 is configured to receive a tool (not shown) for opening the ligating slide 14. The tool, such as a Spin Tek™ tool from Ormco Corporation or a similar tool (the tool may be configured for access to the lingual surface of a tooth) may therefore be inserted into the tool recess 112 in a direction that is generally aligned with the archwire slot 16. Rotation of the tool by 90° from the direction of insertion leverages the tool against the bracket body 12 at or near the slot surface 40 and pushes the slide 14 toward the opened position. The recess 110 is dimensioned to communicate with the tool recess 112 so that the tool clears the bracket body 12 as the slide 14 is moved toward the opened position and allows the tool to be fully rotated to 90° from its orientation upon insertion into the tool recess 112. The relative position of the recess 110 and the tool recess 112 is shown best in FIG. 8A.

Additionally, in one embodiment, and with reference to FIG. 7, the bracket body 12 may include a gingival tie wing 114. The ligating slide 14 may also include a tie wing 116. It will be appreciated that the opposing tie wings 114, 116 may provide a region in which the clinician may engage a ligature, for example, to provide additional pressure on the slide 14 to maintain it against the bracket body 12 and in the closed position during treatment.

As introduced above, in one embodiment, and as illustrated in FIG. 3, the resilient member 20 may be generally tubular having a circular cross section. The cross section may be continuous, that is, the tubular resilient member 20 may be without slots or other discontinuities in its sidewall. In this regard, and unlike a slotted tubular spring pin, the perimeter of the resilient member 20 is generally maintained when the resilient member 20 is elastically deformed. The member 20 may be dimensioned to fit within the bores 92, 94 and through the aperture 52. In an exemplary embodiment, the resilient member 20 may be composed of Nickel Titanium (NiTi) superelastic material. By way of example, one NiTi composition includes about 55 wt. % nickel (Ni), and about 45 wt. % titanium (Ti) with minor amounts of impurities and which is available from NDC of Fremont, Calif. The mechanical properties of the NiTi alloy may include an ultimate tensile strength of greater than about 155 ksi, an upper plateau of greater than about 55 ksi, and a lower plateau of greater than about 25 ksi. The dimensions of the resilient member 20 may vary depending on the size of the bracket itself. In one embodiment, the resilient member 20 is a generally right circular hollow cylinder having an axis 118 and a diameter of about 0.016 inches and being from about 0.50 inches to about 0.125 inches in length. The wall thickness may measure from about 0.001 inches to about 0.004 inches, and may preferably be about 0.002 inches to about 0.003 inches. During assembly, the resilient member 20 may be press fit or slip fit into bores 92, 94, and/or may be secured therein to prevent relative movement therebetween using various processes including staking, tack welding, laser welding, adhesives, or other suitable methods.

During use, and as is illustrated in the sequence of FIGS. 8A-8D, when the ligating slide 14 is in the opened position, the resilient member 20 may be positioned within the first lobe portion 56 (labeled in FIG. 5) of the aperture 52. The common axis 95 of each of the bores 92, 94 may be aligned with the axis 58 of the first lobe portion 56. The axis 118 of the resilient member 20 may also be aligned with the axis 58 depending on the cross-sectional dimensions of the resilient member 20. Generally, in this position, and where each of the first lobe portion 56 and bores 92, 94 are generally larger in dimension than the resilient member 20, the resilient member 20 is in a relaxed, undeformed state and may not bias the ligating slide 14 in any given direction. However, the resilient member 20 may resist external forces acting on the slide 14 in a direction indicated by arrow 120 in FIG. 8A.

Figure 8A:
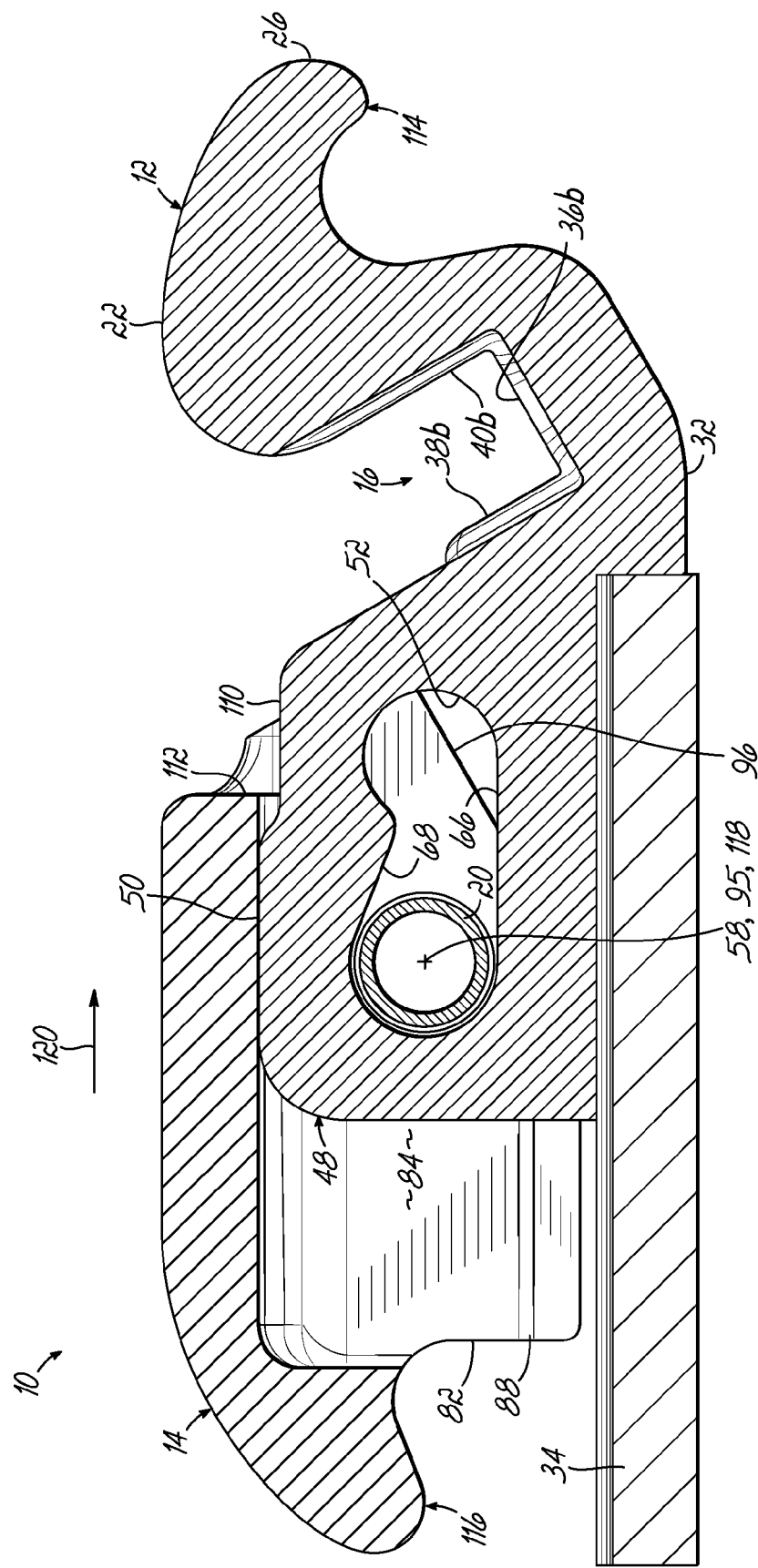
FIG. 8A is a cross-sectional view of the orthodontic bracket taken along section line 8-8 of FIG. 2, depicting the slide member in the opened position.

For example, where the bracket 10 is mounted on the lingual surface of a lower anterior tooth (as shown in FIG. 1), gravity will tend to pull the slide 14 toward the closed position or in the direction of the arrow 120 in FIG. 8A. Because the central portion 64 includes the segment 68, which provides a gradually decreasing clearance dimension that is less than the outside diameter of the resilient member 20, the central portion 64 interferes with movement of the resilient member 20 in the direction indicated by arrow 120. Advantageously, interference between the segment 68 and the resilient member 20 limits the distance that gravity may move the slide 14. The slide 14 therefore remains substantially in the opened position. It will be appreciated that a clinician, after positioning the slide 14 in the opened position, may remove an existing archwire from the archwire slot 16 and insert another archwire into the archwire slot 16 without concern that the ligating slide 14 will spontaneously move toward the closed position under the influence of gravity.

Additionally, cooperation between the member 20 in the aperture 52 may require intentional application of force to close the slide 14. A minimum threshold force may be required on the slide 14 to move it toward the closed position. In one embodiment, the minimum threshold force is greater than the sliding weight of the slide 14. In this embodiment, only when the force on the slide 14 exceeds the minimum threshold force does the resilient member 20 move toward the closed position. Forces on the slide 14 that exceed the minimum threshold force cause the resilient member 20 to elastically deform. Elastic deformation of the resilient member 20 is dictated by the shape of the central portion 64 of the aperture 52. In this regard, elastic deformation of member 20 may be localized to a region of contact with the aperture 52. By elastic deformation, the strain produced in the resilient member 20 is fully recovered, and the member 20 reverts to its original shape, upon removal of the deforming force.

Figure 8B:
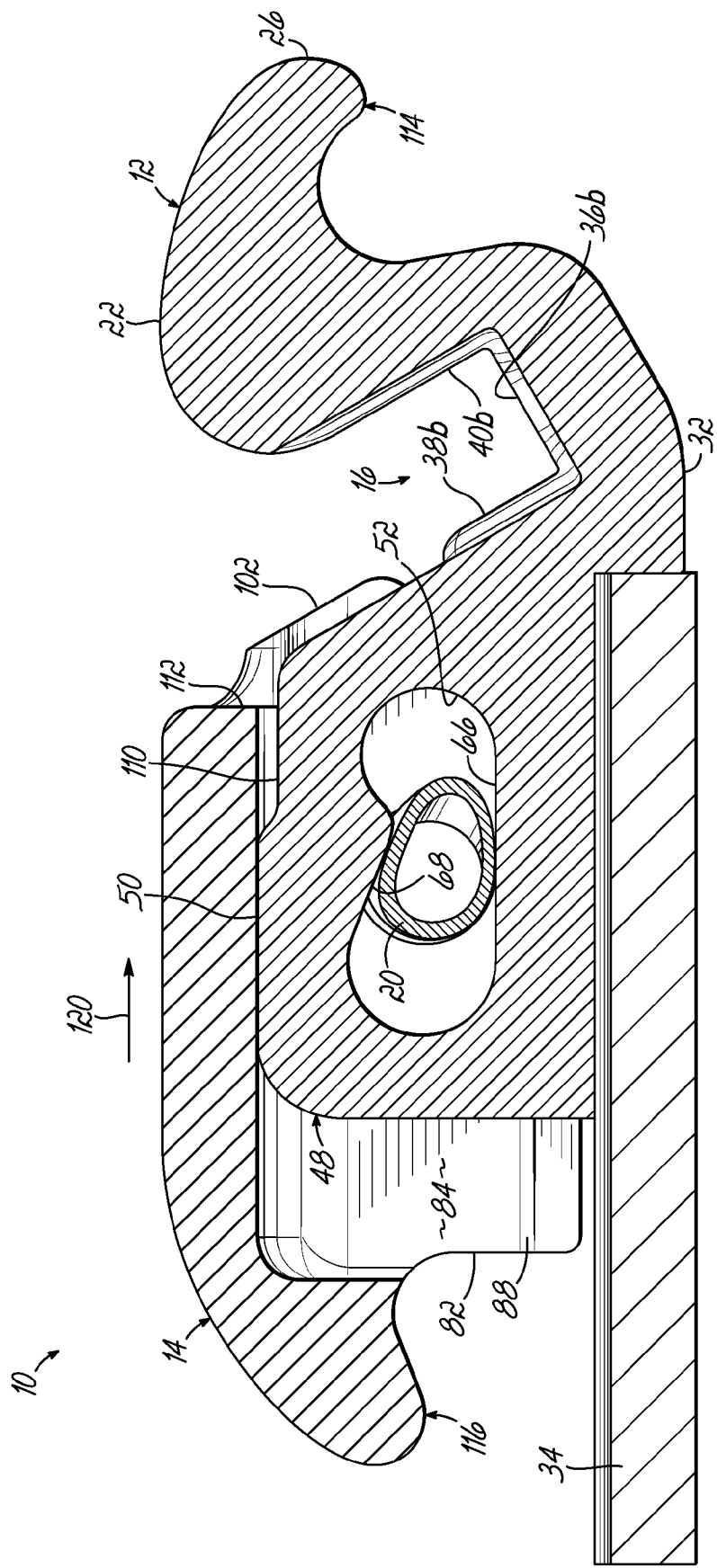
FIG. 8B is a cross-sectional view of the orthodontic bracket taken along section line 8-8 of FIG. 2, depicting the slide member in a position between the closed position of FIG. 1 and the opened position shown in FIG. 2.

FIG. 8B depicts an exemplary embodiment in which a force on the slide 14 exceeds the minimum threshold force required to move the slide 14 toward the closed position. Where the force on the slide 14 is sufficient to cause elastic deformation of the resilient member 20, the slide 14 may be moved toward the closed position. It will be appreciated that depending on the configuration of the second segment 68, a gradually increasing force may be required to continuously move the slide 14 along the slide track 70 toward the closed position. The rate at which the force is required to increase is dictated by the shape of the central portion 64 and the properties of the resilient member 20.

For the exemplary embodiment shown in FIG. 8B, the second segment 68 is a generally planar surface and is believed to require a generally linear increase in force on the slide 14, at least over a portion of the opening movement, to deform the resilient member 20 as shown. The resilient member 20 may deform in a manner which allows it to conform to the shape defined by the distances between the region of contact between the resilient member 20 and the first segment 66 and the region of contact between the resilient member 20 and the second segment 68. As shown, the resilient member 20 may elastically deform by a change in the cross-sectional profile of the member 20. This may include a change to a roughly egg-shaped cross section in the region of contact between the resilient member 20 and the aperture 52. Portions of the resilient member 20 outside of the aperture 52 may not significantly elastically deform and thus retain their original cross-sectional profile. For example, the portions of the resilient member 20 in the bores 92, 94 may remain substantially circular. Thus, elastic deformation of the resilient member 20 may be localized to discrete regions of the resilient member 20 in sliding contact with the aperture 52. It will be appreciated that embodiments of the invention are not limited to any particular form or shape of the resilient member 20.

Figure 8C:
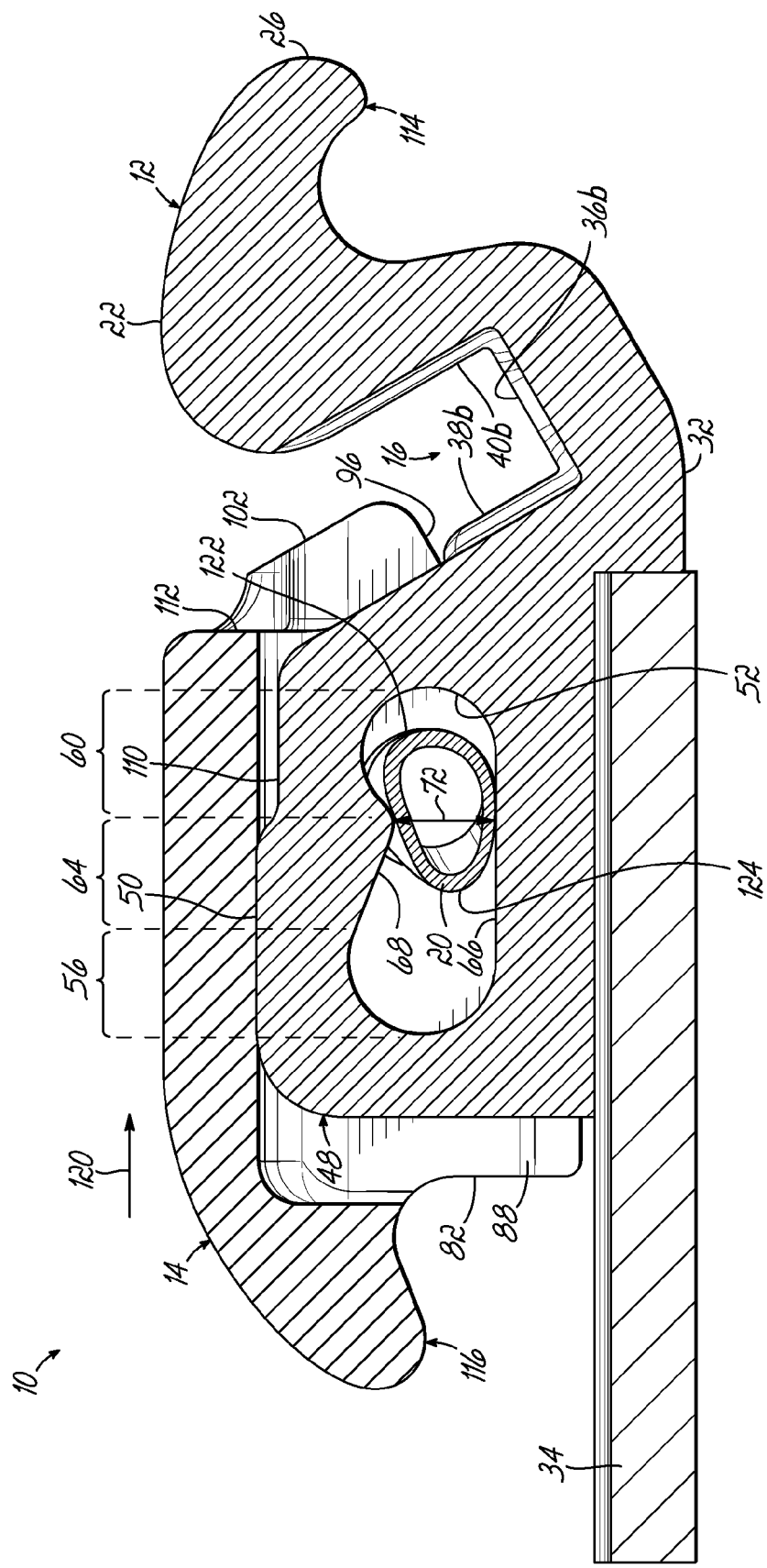
FIG. 8C is a cross-sectional view of the orthodontic bracket taken along section line 8-8 of FIG. 2, depicting the slide member in a position different from the position shown in FIG. 8B between the closed position of FIG. 1 and the opened position shown in FIG. 2.

With reference to FIG. 8C, the ligating slide 14 is moved closer to the closed position under a force greater than the force required to deform the resilient member 20 as shown in FIG. 8B. At some force greater than the threshold force required to initially move the slide 14 towards the closed position, the force applied to the slide 14 is sufficient to conform the resilient member 20 to the dimension of the pinch point 72. At this magnitude of force, the resilient member 20 is elastically deformed in the region of contact with the aperture 52 so that the resilient member 20 may at least partially squeeze through the pinch point 72. As shown, the resilient member 20 may elastically deform to an egg-shaped cross section. At the pinch point 72, a leading portion 122 of the resilient member 20 may reside within the second lobe portion 60 while a remaining portion 124 of the resilient member 20 extends into the central portion 64. The resilient member 20 may reside partially in each of the second lobe 60 and the central portion 64. By way of example and not limitation, the force required to move slide 14 to a position where the resilient member 20 partially enters the second lobe portion 60 may exceed about 0.1 kgf (kilogram force), and by way of additional example, this force may be from about 0.2 kgf to about 0.8 kgf or from about 0.5 kgf to about 0.7 kgf, preferably about 0.6 kgf.

With reference to FIGS. 8A-8C, the magnitude of the force required to overcome the threshold force and/or the threshold sliding force as the ligating slide 14 moves away from the opened position depends on the configuration of the aperture 52. This force may therefore be selectively varied by changing the configuration of the aperture 52. In this regard, the angle of intersection between the second segment 68 and the first segment 66 may be increased to provide a desired opening force and/or sliding force and the rate at which that force may be increased. Furthermore, the position of the pinch point 72 may be selected to provide a shorter or longer central portion by which the rate of force increase may be changed. The shape of the first and/or second segments 66, 68 may be generally planar to provide a linearly increasing sliding force when the resilient member 20 in the central portion 64. Alternatively, one or both of the segments 66, 68 may be contoured or curved (not shown) to provide a variable sliding force. The above-described methods for varying the opening and/or sliding force are exemplary.

Figure 8D:
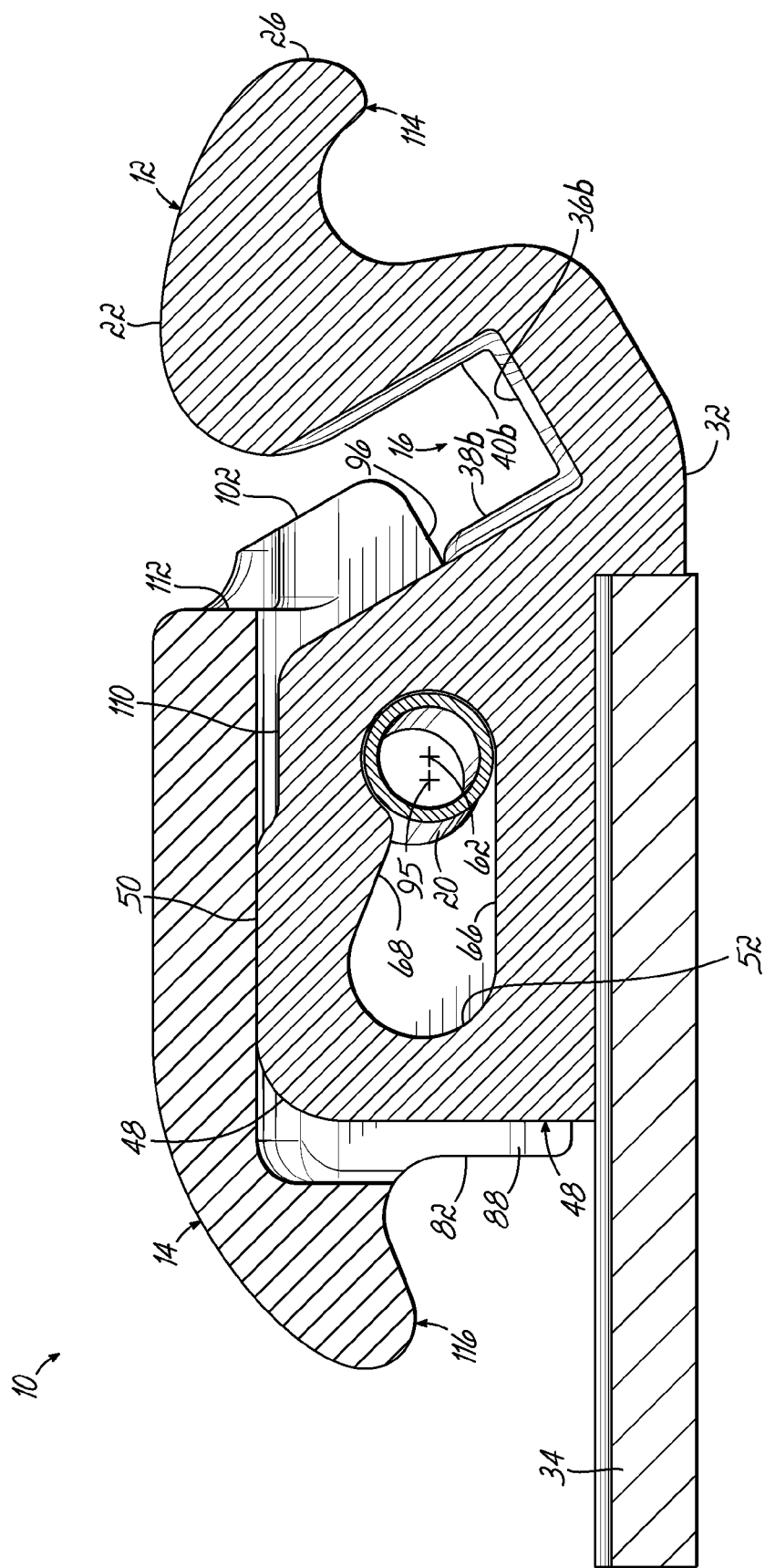
FIG. 8D is a cross-sectional view of the orthodontic bracket taken along section line 8-8 of FIG. 2, depicting the slide member in the closed position.

Referring now to FIG. 8D, once the opening and/or sliding force meets or exceeds the force required to move the resilient member 20 to a position that is at least partially through the pinch point 72, the resilient member 20 may spontaneously slide or move the remainder of the distance into the second lobe portion 60. That is, the leading and remaining portions 122, 124 may spontaneously move into the second lobe portion 60 in the absence of additional external force. More specifically, once a threshold proportion of the resilient member 20 enters the second lobe portion 60, the sliding movement of the resilient member 20 into the second lobe portion 60 may proceed spontaneously. This movement may be accompanied by an audible and/or a tactile "click" or "snap" when the resilient member 20 expands into the second lobe portion 60. By this feature, the clinician may then be assured that the ligating slide 14 has reached its closed position and will remain in the closed position under normal forces observed during the orthodontic treatment.

It is believed that the elastic nature of the resilient member 20 causes a natural inclination for the resilient member 20 to return to an undeformed or at least a less deformed configuration than the deformed configuration of the resilient member 20 in the vicinity of the pinch point 72. Thus, when a threshold portion of the resilient member 20 enters the second lobe portion 60 of the aperture 52, the member 20 may spontaneously release internal elastic energy (by virtue of its deformed condition). Such a release causes the resilient member 20 in the vicinity of the pinch point 72 to move into and fill the second lobe portion 60 without application of additional external force. In other words, only a fractional portion of the resilient member 20 may enter the second lobe portion 60 when an external force is applied to the slide 14 to move the slide 14 to the pinch point 72. The resilient member 20 may move the remainder of the distance into the second lobe portion 60 to revert to a configuration having less or no elastic deformation.

In one embodiment, should an insufficient force be applied to the resilient member 20 so that it fails to enter the second lobe portion 60, the slide 14 may move, in the absence of an external force, toward the opened position because the resilient member 20 may gradually expand into the larger regions of the central region 64 proximate the first lobe portion 56. Ultimately, the resilient member 20 may enter the first lobe portion 56.

Figure 9:
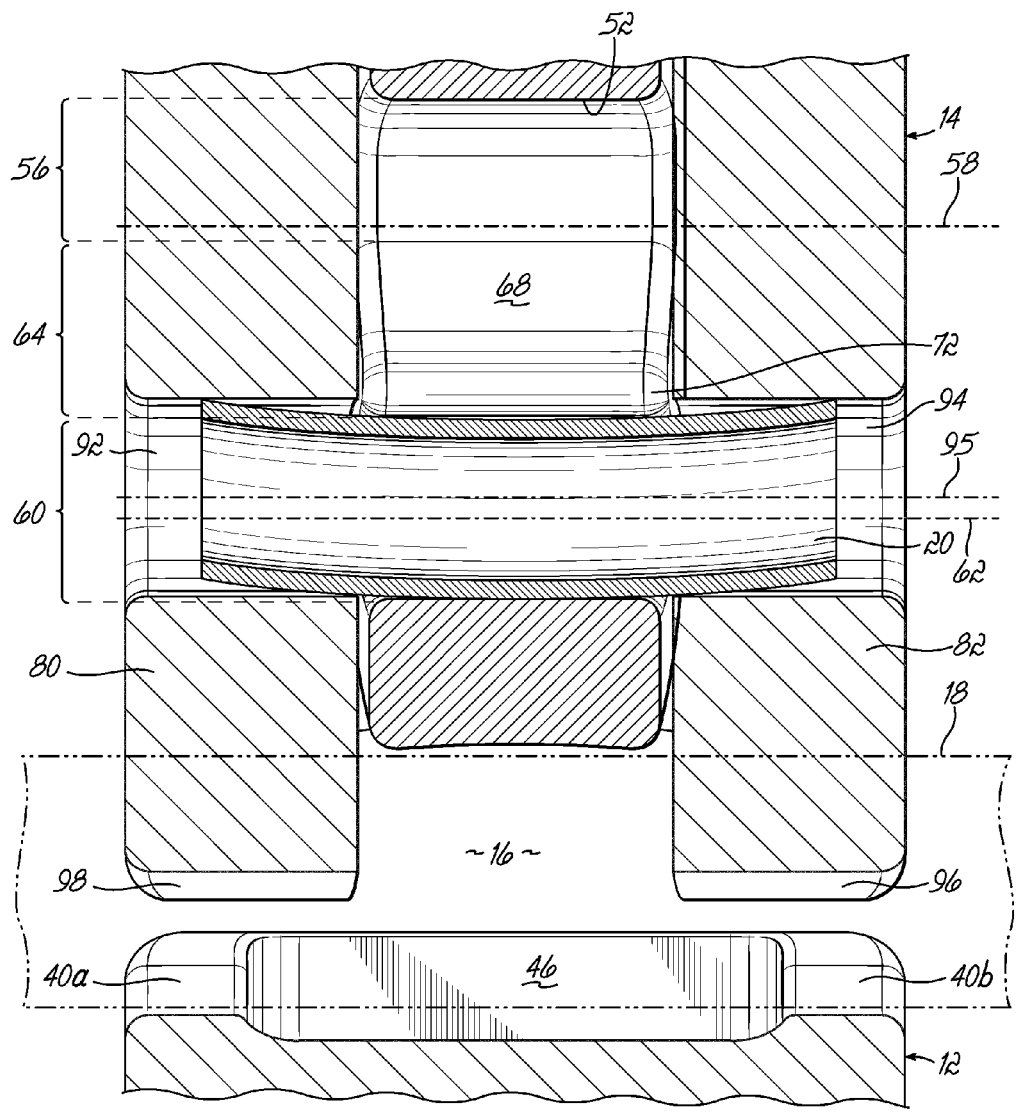
FIG. 9 is a cross-sectional view of the orthodontic bracket shown in FIG. 2 taken along section line 9-9.

In one embodiment and with reference to FIGS. 8D and 9, the ligating slide 14 is shown in the closed position. However, the bores 92, 94 are not fully aligned with the second lobe portion 60 of the aperture 52. In particular, while the slide 14 is in the closed position, the bores 92, 94 are offset from the second lobe portion 60. The offset may be in the occlusal direction or in a direction away from the archwire slot 16.

In one embodiment, the axis 95 of the bores 92, 94 is at a greater distance from the archwire slot 16 than the axis 62 of the second lobe portion 60. Nevertheless, even with an offset relationship, the resilient member 20 may spontaneously expand into the second lobe portion 60 to release some of the elastic deformation produced by the pinch point 72. That is, less than 100% of the elastic deformation may be released. As a result, when in the second lobe portion 60, the resilient member 20 may be elastically deformed along its axis 118, due to the offset between axis 62 and 95, as is shown in FIG. 9. It is believed that lack of alignment when the bores 92, 94 are offset from the second lobe portion 60 causes the resilient member 20 to be bowed or curved. So, while the resilient member 20 may spontaneously expand into the second lobe portion 60, to release the stored elastic deformation energy from forced movement from the opened position to the pinch point 72, the resilient member 20 may retain some elastic deformation in the closed position. However, the amount of elastic deformation may be less than the amount observed at the pinch point 72.

As set out above, once the slide 14 is in the closed position (FIG. 8D), the elastic deformation in the resilient member 20 produces a bias in the slide 14 in the direction of motion of the slide 14, for example, in the direction of the archwire slot 16. The bias in the resilient member 20 must be overcome before the slide 14 is movable toward the opened position. Because the applied force must first overcome the bias that is the result of elastic deformation of the resilient member 20, the resilient member 20 provides more consistent contact between the slide 14 and the bracket body 12. For example, the bias may provide more consistent contact between the engagement surfaces 96, 98 and the shoulders 74, 76. Advantageously, the depth of the archwire slot 16 in the generally labial-lingual direction is determined by the position of the shoulders 74, 76 relative to the base surface 36 of the archwire slot 16. Due to the biasing of the ligating slide 14 against shoulders 74, 76 other tolerance variations may no longer have a bearing on the close fit between the archwire slot lumen and the archwire 18.

Figure 10:
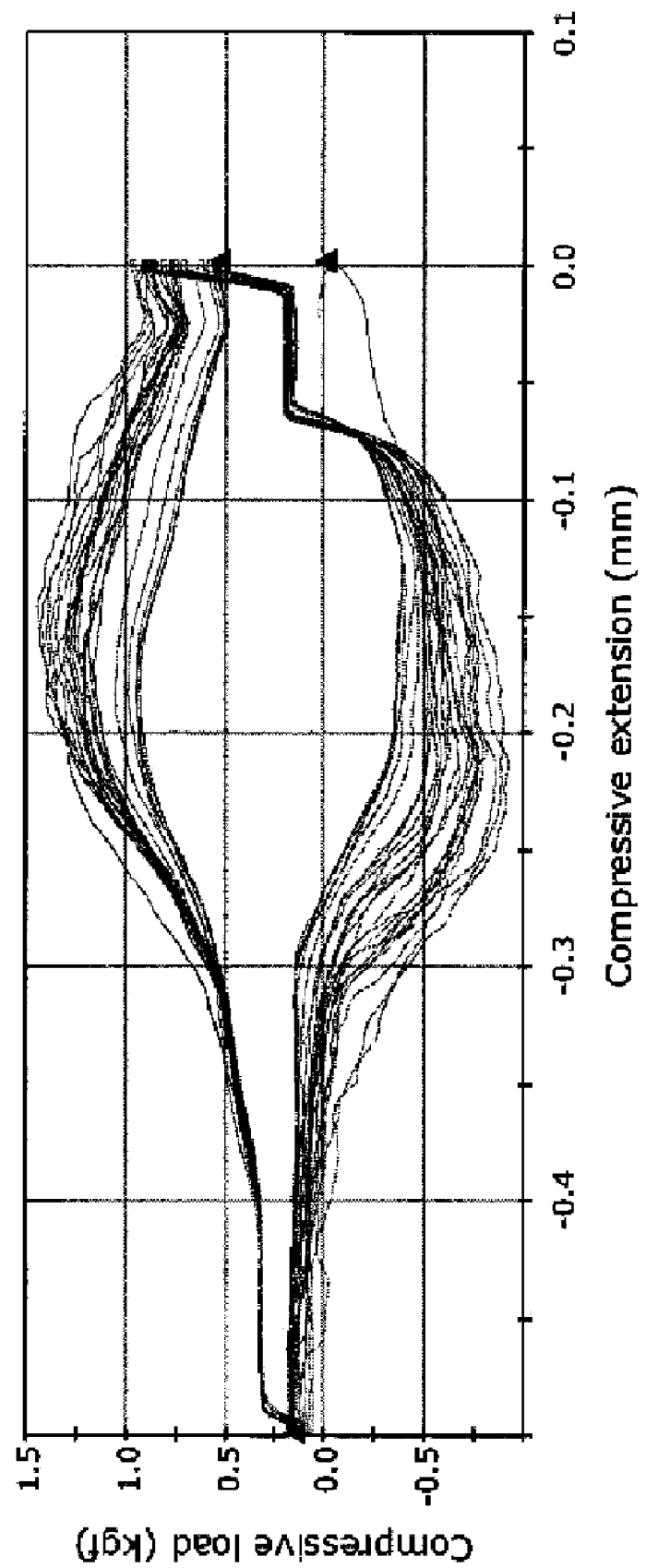
FIG. 10 is a graph of compressive extension versus compressive load for the opening and closing of the slide member according to one embodiment of the invention.

FIG. 10 illustrates data representing the forces required to move a slide member according to one embodiment of the invention from the opened to the closed position. A machine available from Instron Corporation, Noorwood, Mass., was used to collect the data illustrated in FIG. 10. Generally, the top curve is compressive load observed during closing of the slide member, the bottom curve is the compressive load observed during opening of the slide member.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. By way of example, while the embodiments described herein show the resilient member pushing the ligating slide in the direction of the slide motion, the resilient members may be configured to pull the ligating slide toward the base surface of the archwire slot.

Thus, the various features of the invention may be used alone or in any combination depending on the needs and preferences of the user.

What is claimed is:

1. An orthodontic bracket for coupling an archwire with a tooth, comprising:
   a bracket body configured to be mounted to the tooth, the bracket body including an archwire slot defined at least in part by a base surface and opposed slot surfaces extending from the base surface, the archwire slot being configured to receive the archwire therein and defining an aperture having a first portion and a second portion;
   a slide member slidable relative to the archwire slot between an opened position and a closed position in which at least a portion of the slide member forms a surface of the archwire slot and including a bore; and
   a resilient member being received in the bore and extending from the bore and into the aperture and being configured to engage the first portion of the aperture when the slide member is in the opened position and the second portion of the aperture when the slide member is in the closed position, the resilient member being configured to impose a biasing force on the slide member in the direction of movement of the slide member toward the archwire slot when the slide member is in the closed position.

2. The orthodontic bracket of claim 1, wherein the resilient member is configured to impose a biasing force on the slide member in the direction of movement of the slide member away from the archwire slot when the slide member is at a position between the opened position and the closed position.

3. The orthodontic bracket of claim 1, wherein the second portion of the aperture is closer to the archwire slot than the first portion.

4. The orthodontic bracket of claim 1, wherein the axis of the portion of the resilient member in the bore is offset from the axis of the portion of the resilient member in the second portion of the aperture when the slide member is in the closed position.

5. The orthodontic bracket of claim 1, wherein a longitudinal axis of the resilient member is substantially parallel to the archwire slot and is at a first distance from the archwire slot when the slide member is in the opened position and the longitudinal axis of the resilient member is at a second distance from the archwire slot when the slide member is in the closed position, the second distance being less than the first distance along the length of the resilient member.

6. The orthodontic bracket of claim 1, wherein the aperture is asymmetric about a plane substantially parallel to the archwire slot.

7. The orthodontic bracket of claim 6, wherein the first portion of the aperture is separated from the second portion of the aperture by a pinch point that squeezes the resilient member during sliding movement thereof.

8. The orthodontic bracket of claim 6, wherein the aperture is asymmetric about a plane bisecting the length of the aperture.

9. The orthodontic bracket of claim 6, wherein the first portion is separated from the second portion by a central portion and a first radius defines the first portion and a second radius defines the second portion, and the central portion includes a first segment and a second segment opposing the first segment, the first segment being tangent to the first radius and tangent to the second radius, the second segment being tangent to the first radius and transverse to the first segment.

10. The orthodontic bracket of claim 9, wherein a projection of the second segment intersects the first segment or a projection thereof at a location between the first portion and the archwire slot and forms an angle with the first segment of equal to or less than about 60°.

11. The orthodontic bracket of claim 9, wherein a projection of the second segment intersects the first segment or a projection thereof at a location between the first portion and the archwire slot and forms an angle with the first segment of between about 10° and about 30°.

12. The orthodontic bracket of claim 1, wherein the resilient member includes a hollow spring pin having a continuous sidewall.

13. The orthodontic bracket of claim 1, wherein the bracket body includes a dovetail-shaped portion and the slide member includes a central portion configured to receive the dovetail-shaped portion, the dovetail-shaped portion and the central portion being configured to form an interference fit that limits movement of the slide member in a direction away from the tooth when the slide member is at least in the closed position.

14. The orthodontic bracket of claim 1, wherein the archwire slot includes a base surface and a first slot surface and a second opposing slot surface that each extends outwardly from the base surface, and the aperture defines a slide track along which the resilient member is slidable, and wherein a projection of the slide track forms an acute angle with the base surface or a projection thereof.

15. The orthodontic bracket of claim 14, wherein the slide member has a leading surface and, when the slide member is in the closed position, a gap is formed between the leading surface and one of the first slot surface and the second slot surface.

16. The orthodontic bracket of claim 14, wherein the bracket body further includes a shoulder that is oriented at a transverse angle relative to the slide track and the slide member abuts the shoulder when the slide member is in the closed position.

17. The orthodontic bracket of claim 16, wherein the shoulder is parallel to the base surface of the archwire slot.

18. The orthodontic bracket of claim 16, wherein the slide member has a leading surface and the slide member abuts the shoulder and prevents the leading surface from contacting an opposing portion of the bracket body.

19. An orthodontic bracket for coupling an archwire with a tooth, comprising:
 a bracket body configured to be mounted to the tooth, the bracket body including an archwire slot configured to receive the archwire therein and defining an aperture having a first portion and a second portion, the first portion being separated from the second portion by a central portion, and the aperture being asymmetric about a plane substantially parallel to the archwire slot, wherein a first radius defines the first portion and a second radius defines the second portion, and the central portion includes a first segment and a second segment opposing the first segment, the first segment being tangent to the first radius and tangent to the second radius, the second segment being tangent to the first radius and transverse to the first segment;
 a slide member slidable relative to the archwire slot between an opened position and a closed position and including a bore; and
 a resilient member being received in the bore and extending from the bore and into the aperture and being configured to engage the first portion of the aperture when the slide member is in the opened position and the second portion of the aperture when the slide member is in the closed position, the resilient member being configured to impose a biasing force on the slide member in the direction of movement of the slide member toward the archwire slot when the slide member is in the closed position.

* * * * *